(12) United States Patent
Drouet et al.

(10) Patent No.: US 6,337,180 B1
(45) Date of Patent: *Jan. 8, 2002

(54) PEPTIDE REAGENT ENABLING A PRIMARY EPSTEIN-BARR VIRUS INFECTION TO BE DETECTED BY TESTING FOR THE CORRESPONDING ANTIBODIES, AND METHOD FOR USING THIS REAGENT

(75) Inventors: Emmanuel Drouet, Corenc; Richard Brebant, Marcy-l'Etoile, both of (FR)

(73) Assignee: L'Universite Joseph Fourier, St Martin d'Heres (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,089
(22) PCT Filed: Jan. 4, 1996
(86) PCT No.: PCT/FR96/00014
§ 371 Date: Aug. 15, 1997
§ 102(e) Date: Aug. 15, 1997
(87) PCT Pub. No.: WO96/21155
PCT Pub. Date: Jul. 11, 1996

(30) Foreign Application Priority Data

Jan. 4, 1995 (FR) .............................................. 95 00036

(51) Int. Cl.⁷ ................................................ C12Q 1/70
(52) U.S. Cl. ........................... 435/5; 530/324; 530/326; 530/327; 436/513
(58) Field of Search .......................... 424/229.1, 230.1; 435/5; 530/324, 326, 327; 436/513

(56) References Cited

U.S. PATENT DOCUMENTS 4,879,213 A * 11/1989 Fox ................................ 435/5
5,122,448 A * 6/1992 Vaughan ........................ 435/5

FOREIGN PATENT DOCUMENTS

EP      A 0154917         9/1985
WO      WO-A 92-000525    1/1992

OTHER PUBLICATIONS

Marechal, V. Et al. "Enzyme–linked immunosorbent assay for antibodies to ZEBRA, an Epstein–Barr trans–activator." *Research in Virology*, vol. 144, No. 5, 1993, pp. 397–404.

Cheng, Hwee–Ming et al. "Epstein–Barr Virus Nuclear Antigen 1 Linear Epitopes That Are Reactive with Immunoglobulin A (IgA) or IgG in Sera from Nasopharyngeal Carcinoma Patients or from Healthy Donors." *Journal of Clinical Microbiology*, vol. 29, No. 10, Oct. 1991, pp. 2180–2186.

Niveleau, A et al. "Grafting peptides onto polystyrene microplates for ELISA." *Journal of Immunological Methods*, vol. 182, 1995 pp. 227–234.

Cheng, Hwe–Ming. "Linear epitopes of the replication–activator protein of Epstein–Barr virus recognised by specific serum IgG in nasopharyngeal carcinoma." *Cancer Immunol Immmunother*, vol. 40, 1995, pp. 251–256.

Tedeschi, R. et al. "The disease associations of the antibody response against the Epstein–Barr virus transactivator protein ZEBRA can be separated into different epitopes." *Journal of General Virology*, vol. 76, 1995, pp 1393–1400.

Joab, I. et al. "Detection of Anti–Epstein–Barr Virus trans–Activator (ZEBRA) Antibodies in Sera from Patients with Human Immunodeficiency Virus." *JID*, vol. 163, Jan. 1991, pp. 53–56.

Joab, I. et al., "Detection of Anti–Epstein–Barr–Virus Transactivator (ZEBRA) Antibodies in Sera from Patients with Nasopharyngeal Carcinoma", *J. Cancer*, vol. 48, 1991, pp. 647–649.

Mikaelian, I. Et al., "The DNA–Binding Domain of Two bZIP Transcription Factors, the Epstein–Barr Virus Switch Gene Product EBI and Jun, Is a Bipartite Nuclear Targeting Sequence", *Journal of Virology*, Feb. 1993, pp. 734–742.

Miller, G., "The Switch between Latency and Replication of Epstein–Barr Virus", *The Journal of Infectious Diseases*, vol. 161, 1990, pp. 833–844.

Brousett, P. et al. "Epstein–Barr virus (EBV) replicative gene expression in tumour cells of AIDS–related non–Hodgkins' lymphoma in relation to CD4 cell number and antibody titres to EBV", *AIDS*, vol. 8, 1994, pp. 583–590.

Mathew, A. et al., "A high incidence of serum IgG antibodies to the Epstein–Barr virus replication activator protein in nasopharyngea carcinoma", *Cancer Immunology Immunotherapy*, vol. 38, 1994, pp. 68–70.

* cited by examiner

Primary Examiner—Donna C. Wortman
(74) Attorney, Agent, or Firm—Oliff & Berridge, PLC

(57) ABSTRACT

The use of a peptide reagent for detecting the presence or absence of a primary Epstein-Barr virus infection in a patient by testing for IgM antibodies, recognizing said reagent, in a biological sample from the patient according to a per se known method based on the formation of at least one antigen-antibody complex, is disclosed. The reagent contains a peptide recognized by at least one antibody to a peptide having the sequence of formula (II): Leu Glu Ile Lys Arg Tyr Lys Asn Arg Val Ala Ser Arg Lys Cys Arg Ala Lys Phe Lys Gln. The reagent enables such a primary infection to be detected very early.

7 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 39 amino acids
      (B) TYPE: amino acid (C) STRANDEDNESS:
            (D) TOPOLOGY: Not Relevant (ii) MOLECULE TYPE: peptide (xi) SEQUENCE DESCRIPTION: SEQ ID NO:1:

Arg Arg Thr Arg Lys Pro Gln Gln Pro Glu Ser Leu Glu Glu Cys Asp
1               5                   10                  15

Ser Glu Leu Glu Ile Lys Arg Tyr Lys Asn Arg Val Ala Ser Arg Lys
            20                  25                  30

Cys Arg Ala Lys Phe Lys Gln
            35

(2) INFORMATION FOR SEQ ID NO:2:

(i) SEQUENCE CHARACTERISTICS:
        (A) LENGTH: 21 amino acids
        (B) TYPE: amino acid
        (C) STRANDEDNESS:
        (D) TOPOLOGY: Not Relevant (ii) MOLECULE TYPE: peptide (xi) SEQUENCE DESCRIPTION: SEQ ID NO:2:

Leu Glu Ile Lys Arg Tyr Lys Asn Arg Val Ala Ser Arg Lys Cys Arg
1               5                   10                  15

Ala Lys Phe Lys Gln
            20

(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS:
        (D) TOPOLOGY: Not Relevant (ii) MOLECULE TYPE: peptide (xi) SEQUENCE DESCRIPTION: SEQ ID NO:3:

Val Ala Ser Arg Lys Cys Arg Ala Lys Phe Lys Gln
1               5                   10

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS:
        (D) TOPOLOGY: Not Relevant (ii) MOLECULE TYPE: peptide (xi) SEQUENCE DESCRIPTION: SEQ ID NO:4:

Ser Glu Leu Glu Ile Lys Arg Tyr Lys Asn Arg Val Ala Ser Arg Lys
1               5                   10                  15

Cys Arg Ala Lys Phe
            20

PEPTIDE REAGENT ENABLING A PRIMARY EPSTEIN-BARR VIRUS INFECTION TO BE DETECTED BY TESTING FOR THE CORRESPONDING ANTIBODIES, AND METHOD FOR USING THIS REAGENT

The invention relates to the use of a peptide reagent enabling a primary Epstein-Barr virus infection to be detected, even at a very early stage, by testing in a biological sample for the possible presence of IgM antibodies that recognize the said reagent. The invention also relates to a method for detecting a primary Epstein-Barr virus infection using such a peptide reagent, as well as to a kit (detection set) enabling this method to be carried out.

The Epstein-Barr virus (abbreviation: EBV) is known to be a virus capable of infecting human epithelial and lymphoid cells. It is established that this virus is the source of infectious mononucleosis (abbreviation: IMN). Primary infection occurs most often during childhood, generally asymptomatically, and the virus thereafter remains present in the body in the latent state. It is estimated generally that more than 95% of adult humans are infected with this virus. In some countries and/or in some social groups, it is possible for primary infection not to take place until the age of adolescence or in the young adult. Among these cases of late primary infection, approximately 50% are acute infections accompanied by symptoms of infectious mononucleosis (IMN).

It is known, moreover, that, in some geographic regions, EBV is closely associated with certain cancers, in particular cancer of the nasopharynx and Burkitt's lymphoma.

In immunosuppressed individuals, and in particular individuals who have undergone organ transplants as well as in patients infected with the HIV virus, a "reactivation" of the virus, that is to say transition from a latency state to a lytic cycle of replication of the virus, is frequently observed. It is known that, in immunosuppressed subjects, reactivation of the virus or primary infection frequently leads to the development of various lymphomas.

The study of EBV infection and the search for methods of serological diagnosis have enabled several viral antigens to be demonstrated: the viral capsid antigens (VCA), the early antigens (EA) and the nuclear antigens (EBNA).

The classical serological diagnosis of EBV infections comprises on the one hand the test for heterophil antibodies (Paul-Bunnell-Davidsohn test), and the test for antibodies against the VCA, EA and EBNA antigens, generally by indirect immunofluorescence. These tests are difficult to carry out, and a certain proportion of false negatives and false positives are observed.

It is currently accepted that the serological profiles can be interpreted unequivocally in some cases, which are reviewed below.

Primary infection is generally followed closely by the appearance of anti-VCA antibodies, and it is accepted that the absence of anti-VCA IgG enables the conclusion to be drawn that the subject has not been infected with EBV. It is accepted, moreover, that, when a serum does not contain anti-VCA, it does not contain other anti-EBV antibodies either.

In individuals who are asymptomatic carriers, that is to say in almost the whole of the population which has been infected with the virus and in which the virus is in the latency state, both anti-VCA and anti-EBNA antibodies are found.

In the case of symptomatic primary infection (IMN), the test for heterophil antibodies (Paul-Bunnell-Davidsohn or PBD test) is generally positive. The presence of anti-VCA IgG is generally found, while anti-EBNA antibodies are absent or are present in only small amounts. The anti-VCA IgGs gradually decrease after primary infection and remain stable throughout the lifetime, while the anti-EBNA antibodies appear later, after several months, before stabilizing.

In relation to the state of knowledge about EBV infections and their diagnosis, there may be mentioned, in particular, J.-M. Seigneurin—Infections à Virus Epstein-Barr [Epstein-Barr Virus Infections]—Editions techniques—Encycl. Méd. Chir. (Paris-France), Maladies Infectieuses, 8-071-A-10, Pédiatrie 4-310-A-30, pp. 1–7 (1993).

It is known, moreover, that a protein called ZEBRA (or EB1 or Zta) performs a fundamental role in the regulation of latency; see, in particular, G. Miller, J. of Infectious Diseases, 161:838–844 (1990) and I. Mikaélian et al., J. Virol., 67:734–742 (1993).

This protein is a transcription factor which performs, in particular, an activating role in the transcription of certain genes and in its own synthesis. The ZEBRA protein is considered to be closely associated with the transition between the latency state and the lytic cycle of the virus, and the test for anti-ZEBRA antibodies has been studied as an indirect marker of a viral reactivation, in particular in HIV-seropositive immunosuppressed subjects; see, for example, I. Joab et al., J. of Infectious Diseases, 163:53–56 (1991) and V. Maréchal et al., Res. Virol., 144:397–404 (1993).

It has now been discovered that anti-ZEBRA antibodies appear very early during primary infections, and that detection of the presence of anti-ZEBRA IgM antibodies enables primary EBV infections to be diagnosed very early. It has been discovered, in addition, that the test for IgM directed against the fragment 157–195 of the ZEBRA protein enables primary infections to be diagnosed without false negatives at a stage at which none of the traditional serological markers give 100% of positive results.

It will be recalled that the sequence 157–195 of the ZEBRA protein is a peptide corresponding to the formula (I) (SEQ ID NO: 1):

> Arg Arg Thr Arg Lys Pro Gln Gln Pro Glu Ser Leu Glu Glu Cys
> Asp Ser Glu Leu Glu Ile Lys Arg Tyr Lys Asn Arg Val Ala Ser
> Arg Lys Cys Arg Ala Lys Phe Lys Gln.

By a systematic study of testing for antibodies directed against various peptides shorter than the peptide of formula (I), and whose sequence is included in the sequence represented by the formula (I), it was noted that IgMs directed against a portion of the carboxy-terminal end of the sequence of formula (I) are detected more especially in primary EBV infections. The sequence of this portion is represented by the following formula (II) (SEQ ID NO: 2):

> Leu Glu Ile Lys Arg Tyr Lys Asn Arg Val Ala Ser Arg Lys Cys
> Arg Ala Lys Phe Lys Gln.

Hence the subject of the present invention is the use as a peptide reagent enabling a primary Epstein-Barr virus infection in a subject to be detected, and in particular detected very early, by testing for IgM antibodies that recognize the said reagent in a biological sample taken from the said subject, according to a method known per se based on the formation of at least one complex of the antigen-antibody type, characterized in that the said reagent contains a peptide recognized by at least one antibody directed against the peptide whose sequence is represented by the formula (II) given above. Bearing in mind the early stage at which the IgMs directed against the peptide of formula (II) appear, the use of the reagent according to the invention also makes it possible to confirm, with less risk of error than by using the methods known hitherto, the absence of a primary EBV infection.

It is hence possible to use, in particular, as a peptide reagent according to the invention, a peptide comprising all or part of the sequence of formula (II), including a peptide whose sequence is shorter than that of formula (II), for example a peptide of formula (III) (SEQ ID NO: 3):

Val Ala Ser Arg Lys Cys Arg Ala Lys Phe Lys Gln, or alternatively a peptide whose sequence is longer than that of formula (II) (for example the peptide of formula (I)), or else a peptide whose sequence comprises a portion of the N-terminal end of the peptide II supplemented, on the N-terminal side, by an adjacent sequence present in the formula (I), for example a peptide of sequence (SEQ ID NO: 4):

Ser Glu Leu Glu Ile Lys Arg Tyr Lys Asn Arg Val Ala Ser Arg Lys Cys Arg Ala Lys Phe.

The subject of the invention is also a method for detecting a primary Epstein-Barr virus infection in a subject, characterized in that the presence of IgM antibodies capable of recognizing the peptide of formula II) (SEQ ID NO: 2):

Leu Glu Ile Lys Arg Tyr Lys Asn Arg Val Ala Ser Arg Lys Cys Arg Ala Lys Phe Lys Gln is tested for, in a manner known per se, in a biological sample taken from the said subject.

Naturally, the presence of IgM antibodies tested for in this way enables the conclusion to be drawn that a primary EBV infection is present, and the absence of the said antibodies enables the conclusion to be drawn that a detectable primary infection is absent.

According to a particular embodiment, the method of the invention is a method in which:

a biological sample taken from the said subject is brought into contact with a peptide reagent under conditions permitting the formation of an antigen-antibody type complex between the said peptide reagent and antibodies which recognize the said reagent, if they are present in the said sample, and the possible presence of such a complex is tested for according to a visualization method known per se, characterized in that the said peptide reagent contains a peptide recognized by at least one antibody directed against the peptide whose sequence is represented by the formula (II) (SEQ ID NO: 2):

Leu Glu Ile Lys Arg Tyr Lys Asn Arg Val Ala Ser Arg Lys Cys Arg Ala Lys Phe Lys Gln, and in that the complexes whose presence is tested for are complexes formed between the said reagent and IgM type antibodies.

In the methods which have just been described, the peptide reagents are, in particular, the ones which have been defined above.

The biological sample is, in particular, a sample of blood serum or another biological fluid, for example cerebrospinal fluid.

The implementation of tests for detecting antibodies using an antigen is well known and hence will not be described in detail here. The antigen can be bound, by adsorption or by covalent bonding, to a solid support (well of a microtitration plate, wall of a tube, plastic bead, latex particles, and the like). When the antigen is bound to microbeads, it is possible to carry out the procedure according to immunofiltration methods, and, with latex particles, agglutination techniques can be used. It is also possible to carry out the procedure, in particular, according to the so-called "sandwich" solid-phase techniques, or alternatively by competition with labelled antibodies specific for the antigen. In the case of the sandwich techniques, the visualization may be performed in a known manner using labelled heterologous anti-(human IgM) antibodies (animal antibodies). It is also possible to use unlabelled heterologous anti-(human IgM) antibodies and to visualize their binding to the IgM, if the latter are present, with labelled antibodies directed against the immunoglobulins of the animal species from which the heterologous antibodies used originate.

The labelling of the antibodies is performed, in particular, by coupling with an enzyme (for example a peroxidase) capable of catalysing a colour reaction. A fluorescent or luminescent label can also be used.

The formation of antigen-antibody type complexes can also be demonstrated without the use of labelled antibodies, for example using electrical measurements (capacity, impedance), in a known manner.

The subject of the invention is also a kit for detecting an Epstein-Barr virus infection, the said kit comprising a peptide reagent and means for visualizing the presence of an antigen-antibody type complex capable of being formed when the said reagent and antibodies possibly present in a biological sample to be analysed are brought into contact with one another, characterized in that, in order to detect a primary infection by the said virus:

the said peptide reagent contains a peptide recognized by at least one antibody directed against the peptide whose sequence is represented by the formula (I) (SEQ ID NO: 1):

Arg Arg Thr Arg Lys Pro Gln Gln Pro Glu Ser Leu Glu Glu Cys Asp Ser Glu Leu Glu Ile Lys Arg Tyr Lys Asn Arg Val Ala Ser Arg Lys Cys Arg Ala Lys Phe Lys Gln, and in that the said means are means capable of visualizing the presence of antigen-antibody type complexes formed by IgM type antibodies with the said reagent.

The examples which follow illustrate the invention.

EXAMPLE 1

Diagnostic tests were performed using as antigen the ZEBRA protein or certain peptides contained in this protein.

The results were compared with those obtained with the classical tests for serological diagnosis.

The classical tests used are the following:

test for heterophil antibodies (PBD test)

test for IgGs directed against the VCA, EA and EBNA antigens by indirect immunofluorescence. Titration of the anti-VCA and anti-EA antibodies was carried out using the P3HR1 and Raji cell lines, subjected to an induction (transition from the latent cycle to the lytic cycle) with a phorbol myristate/butyrate mixture, respectively. Titration of the anti-EBNA antibodies was performed using the Raji line (uninduced). The P3HR1 and Raji lines are available from numerous laboratories and from the ATCC.

Two commercial kits permitting an immunoenzymatic visualization were used in addition:

the test marketed under the name "Biotest anti-EBV recombinant" by Biotest AG (Germany) to test for anti-EA and anti-EBNA antibodies, and the test marketed under the name "Enzygnost" by Behring (Germany) which permits a test for anti-EBV IgG and IgM antibodies.

In all cases, the sera studied were adsorbed on the reagent Gull-Sorb (Gull Laboratories, Salt Lake City, USA) in order to avoid interference due to rheumatoid factor.

Definitions

A primary EBV infection is defined by the presence of anti-EBV IgM, and especially of anti-VCA IgM, by indirect immunofluorescence and/or by the presence of heterophil antibodies. The presence of anti-VCA IgG (>1:20) and of anti-EA IgG (>1:10) is thereafter observed successively as the infection regresses, with an absence of anti-EBNA antibodies (<1:10).

A reactivation of the EBV virus (secondary infection) is defined by the presence of anti-VCA (>1:320) and anti-EA (>1:40) antibodies, with the presence (or pre-existence when it has been possible to establish it) of anti-EBNA antibodies (>1:10).

A latent infection is defined by the absence of anti-VCA IgM and the absence of anti-EA IgG (<1:10), with the presence of anti-VCA (<1:320) and anti-EBNA IgG.

Peptides used as Antigens

The peptide of formula (I) was synthesized according to traditional methods. This peptide is called here P130.

The ZEBRA protein cloned into *Escherichia coli* was also used as antigen. After bacterial culture, the ZEBRA protein is extracted and purified according to standard techniques.

Immunoenzymatic Reaction

The cups (wells) of microtitration plates are coated with the antigen in the following manner: the peptide is applied to each well in the proportion of 100 ng/100 μl (diluted in 50 mM carbonate-bicarbonate buffer, pH 9.6) and the plate is left to incubate overnight at 37° C.

The plates are then washed 3 times with phosphate-0.1% Tween buffer (PBST) pH 7.4. The sera are diluted to 1/100 in PBS (1M NaCl)-5% foetal calf serum-0.1% Tween buffer (PBSST). The serum thus diluted is applied to the wells in the proportion of 100 μL/well. After incubation for 1 hour at 37° C. followed by 3 washes with PBST, 100 μL of anti-human IgG/peroxidase (or anti-human IgM/peroxidase) conjugate are added. These conjugates, marketed by Jackson-Immunoresearch Inc., are diluted beforehand to 1:26,000 in PBST. After incubation for 30 minutes at 37° C. followed by washing with PBST, the procedure for visualization of the enzyme is carried out for 10 minutes, protected from light, using a solution of tetramethylbenzidine (0.5%) and hydrogen peroxide (0.05%) in citrate buffer pH 4 (100 μl/well). The colour reaction is stopped using 1N sulphuric acid solution. Reading is carried out in a spectrophotometer and the absorbance is measured at 450 nm ($A_{450}$).

Each dilution of serum is tested in duplicate, on the one hand against the antigen (peptide or purified ZEBRA protein), and on the other hand against cups without antigen (control well). The final value adopted for the absorbance is hence the value resulting from the difference between the mean absorbance of the wells containing the antigen and the mean absorbance of the control wells.

Positive reference sera (pool of 10 sera of patients with IMN) and negative reference sera (pool of 20 sera of seronegative and asymptomatic patients) are also tested in duplicate and under the same conditions as the clinical samples.

The threshold value of the absorbance was fixed at 0.200 for the ELISA method using the peptide formula (I) and at 0.300 for the ELISA method using the ZEBRA protein.

20 sera originating from patients with infectious mononucleosis were tested. Anti-P130 IgMs are detected in 100% of the sera, and anti-ZEBRA IgMs in 55% of the cases.

Anti-P130 and anti-ZEBRA IgGs are detected in 75% and 80% of the cases, respectively. Anti-VCA, anti-EA and anti-EBNA IgG antibodies are detected by immunofluorescence in 100%, 100% and 0% of the cases, respectively.

The anti-EA IgMs, anti-EA IgGs and anti-EBNA IgGs were, moreover, tested for with the Biotest test. The results are positive in 90%, 80% and 0% of the cases, respectively.

With the Behring anti-EBV ELISA test, the IgMs and IgGs were detected in 80% and 100% of the cases, respectively.

In 6 other cases studied of patients who seemed to present symptoms of IMN with an absence of anti-VCA, anti-EA and anti-EBNA antibodies by immunofluorescence, anti-EA IgMs (Biotest ELISA test) were detected in 4 patients out of 6, as were anti-EBV IgMs (Enzygnost), while anti-P130 IgMs were detected in all the cases.

Thus, on the collective sera tested (IMN or IMN-like syndrome), only the tests performed with the P130 antigen enabled a primary infection, and even undeclared infections for which the immunofluorescence tests gave negative results, to be detected, while the commercial ELISA tests did not detect all the positive sera detected with P130.

EXAMPLE 2

Use of the Antigen of Formula (II) or of Formula (III)

These peptides were synthesized in a traditional manner. With these peptides, ELISA tests were carried out in a manner similar to that described in Example 1.

The results are similar to those observed with the peptide of formula (I).

What is claimed is:

1. A method for detecting a primary Epstein-Barr virus infection in a subject, comprising:
   obtaining a biological sample from a subject suspected of having a primary Epstein-Barr virus infection; and
   testing the sample for the presence of IgM antibodies that bind to a peptide of SEQ ID NO: 2:

Leu Glu Ile Lys Arg Tyr Lys Asn Arg Val Ala Ser Arg Lys Cys Arg Ala Lys Phe Lys Gln, wherein the presence of said IgM antibodies indicates the presence of a primary Epstein-Barr virus infection.

2. A method for detecting a primary Epstein-Barr virus infection in a subject, comprising:

obtaining a biological sample from a subject suspected of having a primary Epstein-Barr virus infection; and testing the sample for the presence of IgM antibodies that bind to a peptide of SEQ ID NO: 2:

Leu Glu Ile Lys Arg Tyr Lys Asn Arg Val Ala Ser Arg Lys Cys Arg Ala Lys Phe Lys Gln, wherein the presence of said IgM antibodies indicates the presence of a primary Epstein-Barr virus infection, and wherein said biological sample taken from said subject is brought into contact with a peptide reagent under conditions permitting the formation of an antigen-antibody complex between said peptide reagent and antibodies which recognize said peptide reagent, if said antibodies are present in said sample; and the possible presence of said complex is tested for using a visualization method, wherein said peptide reagent only binds to antibodies directed against the peptide of SEQ ID NO: 2:

Leu Glu Ile Lys Arg Tyr Lys Asn Arg Val Ala Ser Arg Lys Cys Arg Ala Lys Phe Lys Gln;

and wherein the complexes whose presence is tested for are complexes formed between said peptide reagent and IgM antibodies, wherein said peptide reagent comprises SEQ ID NO: 1, or comprises a fragment of SEQ ID NO: 1 that binds to antibodies directed against SEQ ID NO: 2.

3. The method according to claim 2, wherein the peptide reagent comprises SEQ ID NO: 2, SEQ ID NO: 3 or SEQ ID NO: 4.

4. The method according to claim 1, wherein said peptide reagent consists of SEQ ID NO: 1, or consists of a fragment of SEQ ID NO: 1 that binds to antibodies directed against SEQ ID NO: 2.

5. The method according to claim 1, wherein the peptide reagent consists of SEQ ID NO: 1, SEQ ID NO: 2, SEQ ID NO: 3, or SEQ ID NO: 4.

6. A peptide consisting of the sequence of SEQ ID NO: 1, SEQ ID NO: 2, SEQ ID NO: 3 or SEQ ID NO: 4, that binds to antibodies directed against SEQ ID NO: 2.

7. A kit for detecting an Epstein-Barr virus infection, comprising a peptide reagent and means for visualizing the presence of an antigen-antibody complex that is formed when said peptide reagent and antibodies, possibly present in a biological sample to be analyzed, are brought into contact with one another, in order to detect, including at an early stage, a primary infection by said virus;

wherein said peptide reagent only binds to antibodies directed against the peptide of SEQ ID NO: 2:

Leu Glu Ile Lys Arg Tyr Lys Asn Arg Val Ala Ser Arg Lys Cys Arg Ala Lys Phe Lys Gln, and wherein said means are able to visualize the presence of antigen-antibody complexes formed between IgM antibodies and said peptide reagent, wherein said peptide reagent consists of all or part of SEQ ID NO: 3.

* * * * *